(12) United States Patent
Liu et al.

(10) Patent No.: US 8,188,302 B2
(45) Date of Patent: May 29, 2012

(54) HYDROAMINATION OF ALKENES

(75) Inventors: Zhijian Liu, Urbana, IL (US); John F. Hartwig, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 685 days.

(21) Appl. No.: 12/251,062

(22) Filed: Oct. 14, 2008

(65) Prior Publication Data

US 2009/0156824 A1 Jun. 18, 2009

Related U.S. Application Data

(60) Provisional application No. 60/979,652, filed on Oct. 12, 2007.

(51) Int. Cl.
*B01J 31/02* (2006.01)
*C07F 9/50* (2006.01)

(52) U.S. Cl. ......................... 549/220; 564/15

(58) Field of Classification Search .................. 549/220; 564/15

See application file for complete search history.

(56) References Cited

U.S. PATENT DOCUMENTS

| | | | |
|---|---|---|---|
| 6,307,087 B1 | 10/2001 | Buchwald et al. | |
| 6,384,282 B2 | 5/2002 | Hartwig et al. | |
| 6,395,916 B1 | 5/2002 | Buchwald et al. | |

OTHER PUBLICATIONS

Liu et al. J. Am. Chem. Soc. 2008, 130, 1570-1571.*
van der Slot et al. Organometallics 2000, 19, 2504-2515.*

Ackermann, L., et al., , "Hydroaminations of unactivated alkenes with basic alkylamines: group 4 metal halide catalysts and Bronsted-ac", "Org. Biomol. Chem.", 2007, pp. 1975-1978, vol. 5.

Beller, M., et al., "Anti-Markonikov Reactions, 6; Rhodium-Catalyzed Amination of Vinylpyridines: Hydroamination versus Oxidative Amination", "Eur. J. Inorg. Chem.", 1999, pp. 1121-1132.

Beller, M., et al. , "The First Rhodium-Catalyzed Anti-Markovnikov Hydroamination: Studies on Hydroamination and Oxidative Amination of Aromat", "Chem. Eur. J.", 1999, pp. 1306-1319, vol. 5, No. 4.

Bender, C. F., et al., "Platinum-Catalyzed Intramolecular Hydroamination of Unactivated Olefins with Secondary Alkylamines", "J. Am. Chem. Soc.", 2005, pp. 1070-1071, vol. 127, No. 4.

(Continued)

*Primary Examiner* — Joseph Kosack
*Assistant Examiner* — Matthew Coughlin
(74) *Attorney, Agent, or Firm* — Blanchard & Associates

(57) ABSTRACT

A method includes reacting an amino group, a composition including rhodium and an organic ligand, and a substrate having structural formula (I) in a reaction mixture.

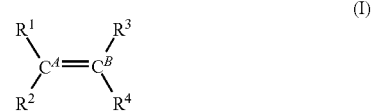

$R^1$ is an organic group including a sp$^3$ carbon atom bonded to $C^A$. $R^2$ is selected from the group consisting of hydrogen, methyl, and an organic group including a sp$^3$ carbon atom bonded to $C^A$. $R^3$ and $R^4$ independently are selected from the group consisting of hydrogen, methyl, and an organic group including a sp$^3$ carbon atom bonded to $C^B$. The method further includes forming a hydroaminated product in the reaction mixture.

5 Claims, 1 Drawing Sheet

OTHER PUBLICATIONS

Casalnuovo, A. L., et al., "Rational Design in Homogeneous Catalysis. Ir(I)-Catalyzed Addition of Aniline to Norbornylene via N-H Activation", "J. Am. Chem. Soc.", 1988, pp. 6738-6744, vol. 110, No. 20.

Coulson, D. R., "Catalytic Addition of Secondary Amines to Ethylene", "Tetrahedron Lett.", 1971, pp. 429-430, vol. 12, No. 5.

Curtin, M. L., et al., "Synthetic and Kinetic Studies of the Intramolecular Diels-Alder Reactions of Cycloalkenylallenylphosphine Oxides", "J. Org. Chem.", 1990, pp. 5278-5287, vol. 55, No. 18.

Dorta, R., et al., "The [IrCl(Diphosphine)]2/Fluoride System. Developing Catalytic Asymmetric Olefin Hydroamination", "J. Am. Chem. Soc", 1997, pp. 10857-10858, vol. 119, No. 44.

Gribkov, D. V., et al., "Hydroamination/Cyclization of Aminoalkenes Using Cationic Zirconocene and Titanocene Catalysts", "Angew. Chem. Int. Ed. Engl.", 2004, pp. 5542-5546, vol. 43.

Hartwig, John F., "Development of catalysts for the hydroamination of olefins", "Pure Appl. Chem.", 2004, pp. 507-516, vol. 76, No. 3.

Johnson, J. S., et al., "Imidotitanium Complexes as Hydroamination Catalysts: Substantially Enhanced Reactivity from an Unexpected Cyclopentadie", "J. Am. Chem. Soc.", 2001, pp. 2923-2924, vol. 123, No. 12.

Kawatsura, M., et al., "Palladium-Catalyzed Intermolecular Hydroamination of Vinylarenes Using Arylamines", "J. Am. Chem. Soc.", 2000, pp. 9546-9547, vol. 122, No. 39.

Lober, O., et al., "Palladium-Catalyzed Hydroamination of 1,3-Dienes: A Colorimetric Assay and Enantioselective Additions", "J. Am. Chem. Soc.", 2001, pp. 4366-4367, vol. 123, No. 18.

Takemiya, A., et al., "Rhodium-Catalyzed Intramolecular, Anti-Markovnikov Hydroamination. Synthesis of 3-Arylpiperidines", "J. Am. Chem. Soc.", 2006, pp. 6042-6043, vol. 128, No. 18.

Utsunomiya, M., et al., "Rhodium-Catalyzed Anti-Markovnikov Hydroamination of Vinylarenes", "J. Am. Chem. Soc.", 2003, pp. 5608-5609, vol. 125, No. 19.

Utsunomiya, M., et al., "Ruthenium-Catalyzed Anti-Markovnikov Hydroamination of Vinylarenes", "J. Am. Chem. Soc.", 2004, pp. 2702-2703, vol. 126, No. 9.

Walsh, P. J. et al., "Stoichiometric and Catalytic Hydroamination of Alkynes and Allene by Zirconium Bisamides", "J. Am. Chem. Soc.", 1992, pp. 1708-1719, vol. 114, No. 5.

* cited by examiner

HYDROAMINATION OF ALKENES

CROSS-REFERENCE TO RELATED APPLICATIONS

This application claims the benefit of U.S. Provisional Application No. 60/979,652 entitled "Catalytic Hydroamination of Amines" filed Oct. 12, 2007, which is incorporated by reference in its entirety.

FEDERALLY SPONSORED RESEARCH OR DEVELOPMENT

The subject matter of this application may have been funded in part under a research grant from the National Institutes of Health, under Grant Number GM 55382. The U.S. Government may have rights in this invention.

BACKGROUND

Alkylamines are among the most common functional groups in pharmaceuticals. The hydroamination of alkenes is one of the simplest and most atom-economical methods to prepare alkylamines, and much effort has now been spent to develop catalysts for such additions of amines to alkenes.

One of the earliest reports of hydroamination was the hydroamination of ethylene with secondary amines, catalyzed by rhodium trichloride (Coulson, D. R. *Tetrahedron Lett.* 12, 429, 1971). A drawback to this approach is that the reaction has only been demonstrated with unsubstituted ethylene, and only when reacted at high temperatures. Most research has been focused on hydroamination of substituted alkenes at temperatures below 100° C.

One approach to hydroamination has been to use activated alkenes. Examples of activated alkenes include alkenes in strained ring systems, such as norbornenes, which have been subjected to hydroamination catalyzed by complexes of transition metals such as iridium (A. L. Casalnuovo et al. *J. Am. Chem. Soc.* 110, 6738, 1988; R. Dorta et al. *J. Am. Chem. Soc.* 119, 10857, 1997). Examples of activated alkenes also include vinyl arenes, which have been subjected to hydroamination catalyzed by complexes of transition metals such as rhodium (Beller, M. et al. *Eur. J. Inorg. Chem.* 1121, 1999; Beller, M. et al. *Chem. Eur. J.* 5, 1306, 1999). Examples of activated alkenes also include allenes, which have been subjected to hydroamination catalyzed by complexes of transition metals such as titanium (Walsh, P. J. et al. *J. Am. Chem. Soc.* 114, 1708, 1992; Johnson, J. S. et al. *J. Am. Chem. Soc.* 123, 2923, 2001.). These reactions have met with mixed success.

Activated alkenes such as vinyl arenes, 1,3-dienes, acrylates and acrylonitriles have been subjected to hydroamination catalyzed by complexes of transition metals such as iron, cobalt, nickel, ruthenium, rhodium, palladium, osmium, iridium, and platinum (Kawatsura, M. et al. *J. Am. Chem. Soc.* 122, 9546, 2000; O. Löber et al. *J. Am. Chem. Soc.* 123, 4366, 2001; Utsunomiya, M. et al. *J. Am. Chem. Soc.* 125, 5608, 2003; Utsunomiya, M. et al. *J. Am. Chem. Soc.* 126, 2702, 2004; Takemiya, A. et al. *J. Am. Chem. Soc.* 128, 6042, 2006). In many cases, these reactions could be performed at room temperature with high yields. Enantioselectivity also could be observed for some systems. A drawback to this approach is that the reactants have included either a vinyl arene or an aromatic amine. Thus, simple alkylamine products have not been reported. Also, hydroamination has been reported only for activated alkenes, in which one carbon of the carbon-carbon double bond was bonded to a $sp^2$ hybridized carbon, such as a ring carbon of an aromatic ring, a carbon of another carbon-carbon double bond, a carbonyl carbon ($>C=O$), or a carbon of a cyano group. The need for an activated alkene limits the scope of substrates that can be used.

Another approach to hydroamination has been to use activated nitrogen sources, instead of amines. Activated nitrogen sources such as sulfonamides, amides and carbamates have been added to vinylarenes, allenes and alkenes. These reactions have been catalyzed by late transition metals, such as iron, palladium, platinum, copper and gold, as well as by protic acids. A drawback to these reactions is that the products do not include simple amino groups, and thus are not alkylamines.

Yet another approach to hydroamination has employed catalytic complexes of lanthanides, actinides, or group IV transition metals such as titanium or zirconium. These catalysts can be highly efficient, and can be used for hydroamination of unactivated alkenes. However, a drawback to this approach is that the catalysts are highly sensitive to air and moisture, and do not have good tolerance of functional groups. Thus, these reactions have not been used widely in the synthesis of complex organic molecules.

It would be desirable to transform unactivated alkenes into alkylamines in a way that is relatively insensitive to air and moisture. It would also be desirable to provide alkylamines from substrates that include one or more functional groups in addition to the alkene group. Ideally, such a system would provide alkylamines from terminal or internal alkenes, using primary or secondary amino groups.

SUMMARY

In one aspect, the invention provides a method including reacting an amino group, a composition including rhodium and an organic ligand, and a substrate having structural formula (I) in a reaction mixture.

(I)

$R^1$ is an organic group including a $sp^3$ carbon atom bonded to $C^A$. $R^2$ is selected from the group consisting of hydrogen, methyl, and an organic group including a $sp^3$ carbon atom bonded to $C^A$. $R^3$ and $R^4$ independently are selected from the group consisting of hydrogen, methyl, and an organic group including a $sp^3$ carbon atom bonded to $C^B$. The method further includes forming a hydroaminated product in the reaction mixture.

In another aspect, the invention provides a composition including rhodium, and an organic ligand selected from the group consisting of 4,5-(bis[bis-diethylamido]-phosphonito)-9,9-dimethylxanthene, 2-dicyclohexyl-phosphino-2'-(N,N-dimethylamino)biphenyl, and substituted derivatives of these.

In yet another aspect, the invention provides a catalyst including rhodium and an organic ligand. When 0.5 millimole (mmol) of 2,2-diphenylpent-4-en-1-amine is combined with the catalyst in 0.5 milliliter (mL) of dioxane to form a reaction mixture, such that the catalyst is present in the reaction mixture in an amount providing 2.5 mole percent (mol %) rhodium relative to the amine, and the reaction mixture is heated at 70° C. for 7 hours, the yield of 1,2-dimethyl-4,4-diphenyl-pyrrolidine is at least 65%.

The following definitions are included to provide a clear and consistent understanding of the specification and claims.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "organic group" means a group containing at least one carbon atom.

The term "amino group" means a group formed by removing a hydrogen from ammonia ($NH_3$), from the nitrogen of a primary amine compound ($RNH_2$) or from the nitrogen of a secondary amine compound (RRNH), where R, R and R are organic groups. A primary amino group may be represented by the structural formula —$NH_2$, and a secondary amino group may be represented by the structural formula —NRH.

The term "alkene" means an acyclic or cyclic compound consisting entirely of hydrogen atoms and carbon atoms, and including at least one carbon-carbon double bond. An alkene may be substituted with one or more substituent groups, which may include atoms other than carbon and hydrogen.

The term "substituent group" means a group that replaces one or more hydrogen atoms in a molecular entity. Examples of substituent groups include halide groups, alkyl groups, heteroalkyl groups, aryl groups, and heteroaryl groups.

The term "substituted derivative" means a compound in which one or more hydrogen atoms has been replaced with a substituent group.

The term "complex" means a molecular entity including a central metal atom, to which is associated a surrounding array of other groups of atoms, referred to as "ligands."

The term "ligand", when referring to a distinct substance, means an organic compound that can be associated to a metal atom when combined with the metal atom.

The term "$sp^3$ carbon atom" means a carbon atom that is bonded to four other atoms through individual single bonds.

The term "heterocyclic group" means a group formed by removing a hydrogen from a ring atom of a heterocyclic compound, where a heterocyclic compound is a cyclic compound having as ring members carbon and at least one other element. Heterocyclic groups include heterocycloalkyl groups, heteroaryl groups, and mixtures of these. A heterocyclic group may be monocyclic or polycyclic and may be substituted with one or more substituent groups.

The term "functional group" means a group that includes atoms other than hydrogen and $sp^3$ carbon atoms, and that has similar chemical properties when it occurs in different organic compounds. Examples of functional groups include hydroxyl (—OH), protected hydroxyl, ether (—C—O—C—), ketone (>C=O), ester (—C(=O)O—C—), carboxylic acid (—C(=O)OH), cyano (—C≡N), amido (—C(=O)NH—C—), protected amino, thiol (—SH), sulfone, sulfoxide, phosphine, phosphite, phosphate, and halide (—X).

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 1:
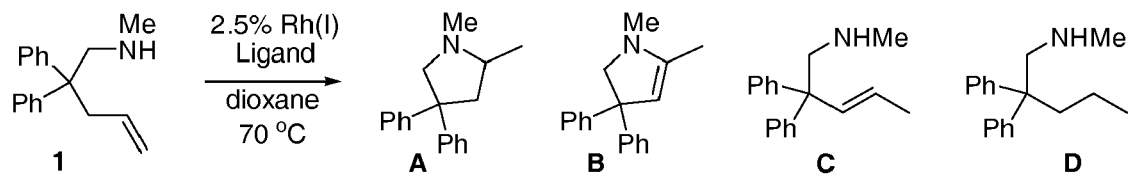
FIG. 1 represents chemical structures and a reaction scheme for an example of hydroamination of the aminoalkene substrate 2,2-diphenylpent-4-en-1-amine (1).

The present invention makes use of the discovery that amines can be added to unactivated alkenes using a composition that includes a rhodium complex. These hydroaminations are mild and can proceed with high yields. Both primary and secondary amines may be added to the alkene. A wide variety of alkene substrates may be used, including 1,1- and 1,2-disubstituted alkenes and alkenes that include other functional groups.

A method may include reacting an amino group, a composition including rhodium and an organic ligand, and a substrate having structural formula (I) in a reaction mixture.

$R^1$ is an organic group including a $sp^3$ carbon atom bonded to $C^A$. $R^2$ is hydrogen, methyl, or an organic group including a $sp^3$ carbon atom bonded to $C^A$. $R^3$ and $R^4$ independently are hydrogen, methyl, or an organic group including a $sp^3$ carbon atom bonded to $C^B$. The reaction mixture may include a solvent, and may include other ingredients. The method further includes forming a hydroaminated product in the reaction mixture.

The substrate includes a carbon-carbon double bond, represented in formula (I) as $C^A = C^B$. In addition to the double bond with $C^B$, carbon $C^A$ is bonded either to two $sp^3$ carbon atoms, or to hydrogen and a $sp^3$ carbon atom. In addition to the double bond with $C^A$, carbon $C^B$ is bonded to two hydrogens, to two $sp^3$ carbon atoms, or to hydrogen and a $sp^3$ carbon atom. For example, referring to structural formula (I), each of $R^2$, $R^3$ and $R^4$ may be hydrogen, such that the double bond is mono-substituted. In another example, $R^2$ is methyl or an organic group including a $sp^3$ carbon atom bonded to $C^A$, and $R^3$ and $R^4$ are hydrogen, such that the double bond is 1,1 di-substituted. In another example, $R^2$ is hydrogen, and one of $R^3$ and $R^4$ is methyl or an organic group including a $sp^3$ carbon atom bonded to $C^B$, such that the double bond is 1,2 di-substituted.

An advantage of this method is that the substrate may include at least one functional group. In conventional hydroamination reactions, functional groups in the substrate can hinder or prevent the desired addition of the amino group. Preferably the substrate may include at least one functional group such as hydroxyl (—OH), protected hydroxyl, ether (—C—O—C—), ketone (>C=O), ester (—C(=O)O—C—), carboxylic acid (—C(=O)OH), cyano (—C≡N), amido (—C(=O)NH—C—), protected amino, thiol (—SH), sulfone, sulfoxide, phosphine, phosphite, phosphate, halide (—X), and combinations of these.

The amino group may be a primary amino group (—$NH_2$) or a secondary amino group (—NRH, where R is an organic group). The compound for which the amino group is a substituent may be, for example, an alkane, a heteroalkane, an alkene, a heteroalkene, or an aromatic compound. The compound may include one or more other substituent groups. Preferably the amino group is a substituent of an alkane or a heteroalkane.

The amino group may be present as part of a compound separate from the substrate, or it may be present as part of the substrate. If the amino group is a substituent group of another compound, separate from the substrate, then a hydroamination reaction between the amino group and the carbon-carbon double bond is an intermolecular reaction. In contrast, if the amino group is a substituent group of the substrate, then a hydroamination reaction between the amino group and the carbon-carbon double bond is an intramolecular reaction.

The hydroaminated product includes a carbon-carbon single bond ($C^A$—$C^B$) in place of the carbon-carbon double bond ($C^A$=$C^B$), and includes an amino group bonded to one of $C^A$ and $C^B$. For intramolecular reactions, the hydroaminated product may include a heterocyclic ring that includes the nitrogen from the amino group and at least one of $C^A$ and $C^B$. Preferably the nitrogen from the amino group, when present in the hydroaminated product, is bonded to a $sp^3$ carbon atom, and optionally to a hydrogen atom. Preferably each of $C^A$ and $C^B$ in the hydroaminated product is bonded to a $sp^3$ carbon atom, and optionally to a hydrogen atom.

The composition including rhodium and an organic ligand may be formed by combining a rhodium complex and the ligand. In this example, the rhodium complex includes a central rhodium atom, one or more ancillary ligands, and optionally one or more counterions. Preferably the rhodium complex includes the central rhodium atom, two or more ancillary ligands and a counterion. Examples of ancillary ligands include cyclooctadiene, cyclooctene, acetonitrile, acetone, and a halide group. Preferred ancillary ligands include cyclooctadiene, cyclooctene and acetonitrile. Examples of counterions include $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$. A preferred counterion is $BF_4^-$.

The organic ligand includes one or more binding groups, which can bind to the rhodium. Examples of binding groups include diphenylphosphino groups (—$PPh_2$), di(cyclohexyl) phosphino groups (—$PCy_2$), di(amido)phosphinato groups (—$P(NR_2)_2$, where R is an organic group), oxo groups (—O—), and tertiary amino groups (—$NR_2$, where R is an organic group). The organic ligand may be monodentate or polydentate, including bidentate, tridentate or tetradentate.

Specific examples of organic ligands include triphenylphosphine ($PPh_3$), tricyclohexylphosphine ($PCy_3$), 1,4-bis(diphenylphosphino)butane (DPPB), bis(2-diphenylphosphinophenyl)ether (DPEphos), 1,1-bis(diphenylphosphino)-ferrocene (DPPF), 9,9-dimethyl-4,5-bis(di-t-butylphosphino)xanthene (t-BuXantphos), 4,5-(bis[bis-diethylamido]phosphonito)-9,9-dimethylxanthene (L1), 2-dicyclohexyl-phosphino-2'-(N,N-dimethylamino)biphenyl (L2), and substituted derivatives of these. Preferably the ligand is DPPF, t-BuXantphos, L1, L2, or a substituted derivative thereof. More preferably the ligand is L1, L2, or a substituted derivative thereof.

The ligand t-BuXantphos may be represented by the following structural formula.

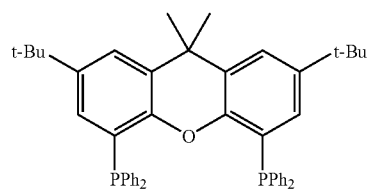

Ligand L1 is an amino analog of the Xantphos ligand. Ligand L1 may be represented by the following structural formula.

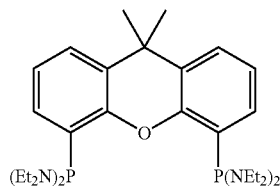

Ligand L2 may be represented by the following structural formula.

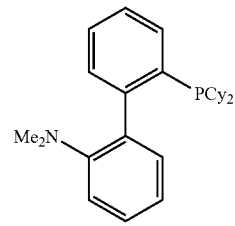

Ligand L2 has been used conventionally for Suzuki cross-coupling (U.S. Pat. Nos. 6,395,916 and 6,307,087). It is commercially available from STREM CHEMICALS, INC. (Newburyport, Mass.).

The relative amounts of rhodium and the organic ligand may be varied. The organic ligand may be present in a stoichiometric excess relative to the rhodium. Preferably the mole ratio of organic ligand to rhodium is from 0.8 to 2. More preferably the mole ratio of organic ligand to rhodium is from 0.9 to 1.5. More preferably the mole ratio of organic ligand to rhodium is from 1 to 1.2.

The reaction mixture may include a solvent. The solvent may be an aprotic solvent, a protic solvent, or a mixture of these. Examples of aprotic solvents include hydrocarbons, such as cyclohexane; aromatic hydrocarbons, such as toluene and xylene; halogenated hydrocarbons, such as dichloromethane; halogenated aromatic hydrocarbons, such as dichlorobenzene; ethers, such as tetrahydrofuran and dioxane; ketones, such as acetone and methyl ethyl ketone; and nitrites, such as acetonitrile. Examples of protic solvents include water and also include alcohols, such as ethanol, isopropanol, cyclohexanol, and glycols and other polyols. Preferably the solvent has a boiling temperature of at least 70° C.

The amount of solvent in the reaction mixture may vary. Preferably, if a solvent is present, there is sufficient solvent to solubilize or disperse the substrate, the amino group, and the composition including rhodium and an organic ligand. In one example, the amount of solvent is from 1 to 100 grams per gram of substrate. It may be desirable to use more or less solvent, or to perform the reaction without solvent.

The reacting may include forming the reaction mixture. The reaction mixture includes the substrate, the amino group, and the composition including rhodium and an organic ligand, and may include a solvent and/or other ingredients. In one example, the reacting includes combining ingredients to form the reaction mixture, where the ingredients include the substrate, the amino group, and the composition including rhodium and an organic ligand. In another example, the reacting includes combining ingredients to form the reaction mixture, where the ingredients include the substrate, the amino group, a rhodium complex, and an organic ligand. In each example, the amino group optionally may be a substituent group of the substrate, and the ingredients optionally may include a solvent.

The reacting may include maintaining the reaction mixture at a temperature of from 25 to 120° C. Preferably the reaction temperature is from 30 to 100° C. More preferably the reaction temperature is from 35 to 90° C., and more preferably is from 40 to 80° C.

The reaction time may be from 1 to 20 hours. Preferably the reaction time is from 2 to 18 hours. More preferably the reaction time is from 3 to 15 hours, more preferably from 5 to 12 hours, and more preferably from 6 to 10 hours.

The hydroaminated product may be recovered from the reaction mixture by typical methods. Examples of recovery methods include extraction, filtration, distillation, crystallization, sublimation, and chromatography. Preferably the yield of hydroaminated product is at least 15%. Preferably the hydroaminated product is the major product. More preferably the yield of hydroaminated product is at least 25%, more preferably at least 50%, more preferably at least 60%, more preferably at least 65%, more preferably at least 70%, more preferably at least 75%, more preferably at least 80%, and more preferably at least 90%.

In an example of the method, a mixture of an aminoalkene (0.50 mmol), a rhodium complex (0.012 mmol), and a bidentate organic ligand (0.015 mmol) in 0.50 mL of dioxane is allowed to stir at 70° C. for 7 hours. The resulting reaction mixture may be washed with brine and extracted with a solvent such as $CH_2Cl_2$. The combined organic fractions may be dried and concentrated under reduced pressure. The residue may then be purified by chromatography to afford the hydroaminated product.

In another example of the method, a reaction mixture including an aminoalkene (0.50 mmol), a rhodium complex (0.005 mmol), and a bidentate organic ligand (0.006 mmol) in 0.50 mL of dioxane is allowed to stir at 70° C. for 7 hours. The reaction mixture may then be washed with brine and extracted with a solvent such as $CH_2Cl_2$. The combined organic fractions may be dried and concentrated under reduced pressure. The residue may then be purified by chromatography to afford the hydroaminated product.

In another example of the method, a reaction mixture of an aminoalkene (0.50 mmol), a rhodium complex (0.025 mmol), and a bidentate organic ligand (0.030 mmol) in 0.50 mL of dioxane is allowed to stir at 100° C. for 10 hours. The reaction mixture may then be washed with brine and extracted with a solvent such as $CH_2Cl_2$. The combined organic fractions may be dried and concentrated under reduced pressure. The residue may then be purified by chromatography to afford the hydroaminated product.

FIG. 1 represents chemical structures and a reaction scheme for an example of hydroamination of the aminoalkene substrate 2,2-diphenylpent-4-en-1-amine (1). Cyclized pyrrolidine product A was the hydroaminated product. The ligands used were DPEphos, DPPB, $PPh_3$, $PCy_3$, DPPF, t-BuXantphos, L1 and L2. The structure of DPEphos is represented below.

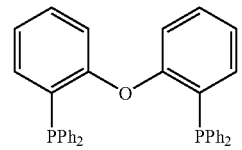

Table 1 lists the reaction yields for different combinations of rhodium complex and organic ligand. Unless otherwise specified, the reaction mixtures were formed with 0.5 mmol of aminoalkene 1, 2.5 mole percent (mol %) of the rhodium complex, and 0.5 mL of dioxane. For entries 1, 2 and 5-11 and 13, the reaction mixtures were formed with 2.5 mol % of the indicated bidentate organic ligand. For entries 3 and 4, the reaction mixtures were formed with 5 mol % of the indicated monodentate organic ligand. The mole percent values were relative to the amount of aminoalkene 1. The reaction mixtures were heated at 70° C. for 7 hours. The yields listed in Table 1 were gas chromatography (GC) yields.

TABLE 1

Effect of Ligand on the Selectivity for Intramolecular Hydroamination of 2,2-Diphenylpent-4-en-1-amine (1)

| | | | Yields of Products Listed in FIG. 1 | | | |
|---|---|---|---|---|---|---|
| Entry | Rhodium Complex | Organic Ligand | % A | % B | % C | % D |
| 1 | $[Rh(COD)_2]BF_4$ | DPEphos | 0 | 0 | 93 | 0 |
| 2 | $[Rh(COD)_2]BF_4$ | DPPB | 10 | 40 | 10 | 30 |
| 3 | $[Rh(COD)_2]BF_4$ | $PPh_3$ | 0 | 0 | 92 | 0 |
| 4 | $[Rh(COD)_2]BF_4$ | $PCy_3$ | 0 | 30 | 30 | 30 |
| 5 | $[Rh(COD)_2]BF_4$ | DPPF | 20 | 30 | 10 | 30 |
| 6 | $[Rh(COD)_2]BF_4$ | t-BuXantphos | 60 | 10 | 10 | 10 |
| 7 | $[Rh(COD)_2]BF_4$ | L1 | 86 | 0 | 0 | 0 |
| 8 | $[Rh(COD)_2]BF_4$ | L2 | 93 | 0 | 0 | 0 |
| 9 | $[Rh(MeCN)_2(COD)]BF_4$ | L2 | 92 | 0 | 0 | 0 |
| 10[a] | $[Rh(COE)_2Cl]_2$ | L2 | 28 | 0 | 0 | 0 |
| 11[a] | $[Rh(COD)Cl]_2$ | L2 | 9 | 0 | 0 | 0 |
| 12[b] | $[Rh(COD)_2]BF_4$ | L2 | 94 | 0 | 0 | 0 |
| 13 | 5% $HBF_4$ | L2 | 0 | 0 | 0 | 0 |

[a]1.25% rhodium was employed with low conversion.
[b]1% of rhodium complex and 1.2% ligand were used.

Reaction of aminoalkene 1 in the presence of 2.5 mol % $[Rh(COD)_2]BF_4$ and 2.5 mol % DPEphos (Table 1, entry 1) formed none of the hydroaminated product (1,2-dimethyl-4,4-diphenylpyrrolidine) (A in FIG. 1). Conventionally, this combination of rhodium complex and organic ligand has been used for the anti-Markovnikov hydroamination of vinylarenes (Utsunomiya, M. et al., *J. Am. Chem. Soc.* 2003, 125, 5608). Instead, the major new species from this reaction resulted from isomerization of the alkene from the terminal to the internal position. Reactions performed in the presence of 2.5 mol % $[Rh(COD)_2]BF_4$ and 2.5 mol % DPPB (Table 1, entry 2) also led to little hydroaminated product A. Conventionally, this combination of rhodium complex and organic ligand has been used for the intramolecular hydroamination of vinylarenes (Takemiya, A. et al., *J. Am. Chem. Soc.* 2006, 128, 6042). Instead, a combination of amine, isomerized alkene, cyclic enamine and the hydroaminated alkylamine A were formed. The hydroaminated product accounted for only 10% of the total reaction product.

Studies with other ligands indicated a strong dependence of the selectivity of the process on the identity of the phosphine. Reactions conducted with PPh$_3$ as ligand gave only isomerized product (Table 1, entry 3). Those conducted with DPPF generated roughly 20% hydroaminated product A (Table 1, entry 5), while those conducted with t-BuXantphos generated roughly 60% of the hydroaminated product A (Table 1, entry 6).

The most selective compositions in this hydroamination were generated from [Rh(COD)$_2$]BF$_4$ and either an amino analog of Xantphos (L1), or a biarylphosphine ligand (L2). Compositions containing these ligands formed the hydroaminated product A as the sole detectable product in 86% and 94% yield by GC (Table 1, entries 7 and 12). The composition generated from L2 and [Rh(MeCN)$_2$(COD)]BF$_4$ was similarly active, while the compositions generated from this ligand and either [Rh(COE)$_2$Cl]$_2$ or [Rh(COD)Cl]$_2$ were less active (Table 1, entries 10 and 11). Reactions in dioxane occurred faster and in higher yield than those in MeCN, THF and toluene. The yield of hydroaminated product A was similar when 1 mol % [Rh(COD)$_2$]BF$_4$ and 1.2 mol % ligand L2 were employed (Table 1, entry 11) as when 2.5 mol % [Rh(COD)$_2$]BF$_4$ and 5 mol % ligand L2 were used. No reaction was observed at this temperature in the presence of acid alone (Table 1, entry 13). Preferred conditions for hydroamination of this aminoalkene using ligand L2 are shown in entry 12 of Table 1.

For the composition formed from [Rh(COD)$_2$]BF$_4$ and L2, a small concentration of active catalyst may be involved in the hydroamination reaction. In hydroamination reactions with this composition, $^{31}$P NMR spectroscopy indicated that the addition of L2 to the rhodium complex provided a solution containing predominantly free ligand, and only 8 mol % of a rhodium-phosphine complex, even after 3 hours at 70° C. However, control experiments confirmed that, in this example, the ligand was necessary to observe hydroamination.

Figure 2:
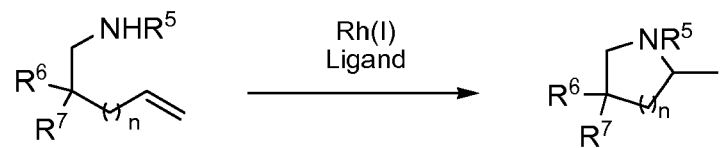
FIG. 2 represents a reaction scheme for a generic example of the hydroamination of FIG. 1.

FIG. 2 represents a reaction scheme for a generic example of the hydroamination of FIG. 1. In FIG. 2, R$^5$, R$^6$ and R$^7$ independently are hydrogen or an organic group. The amino group in the aminoalkene substrate may be a primary amino group or a secondary amino group. The alkenamine substrate may be unsubstituted, or it may be substituted with an alkyl group, a heteroalkyl group, or an aromatic group. In one example, R$^5$ may be hydrogen, an alkyl group or a benzyl group; R$^6$ and R$^7$ independently may be hydrogen, an alkyl group or a phenyl group; and n may be 1 or 2.

Table 2 represents chemical structures of substrates, their corresponding hydroaminated products, and reaction yields for a variety of hydroamination reactions in which the amino group is a secondary amino group. Unless otherwise specified, the reaction mixtures were formed with 0.5 mmol of the aminoalkene, 2.5 mol % of rhodium complex [Rh(COD)$_2$]BF$_4$, 3 mol % of L2 and 0.5 mL of dioxane, and the reaction mixtures were heated at 70° C. for 7 hours. Experimental details are provided in Example 3. The yields listed in Table 2 are isolated yields, for an average of two reactions.

The reactions listed in Table 2 helped to illustrate the scope of the hydroamination of 5- and 6-N-alkyl aminoalkenes to form nitrogen heterocycles. A variety of 5-aminoalkenes underwent hydroamination to generate the corresponding hydroaminated product in excellent yields (Table 2, entries 1-10). Generation of high yields of hydroaminated products was observed not only for N-methyl aminoalkenes, but also more bulky secondary amines, such as N-cyclohexylmethyl and N-benzyl amines (Table 2, entries 1-3).

Surprisingly, many functional groups, such as halides, ethers, nitriles, and esters, were tolerated (Table 2, entries 4-7). Perhaps most remarkable, reaction of the substrate in entry 10 of Table 2, which contained an allylic alcohol function, occurred in good yield with high diastereoselectivity, without significant decomposition of the alcohol or deactivation of the rhodium. This was the first demonstration that a free hydroxyl group could be tolerated during alkene hydroamination. In a similarly surprising way, the reaction of N-(4-methoxybenzyl)-2,2-diphenylpent-4-en-1-amine (substrate in Table 2, entry 5) occurred in 90% yield, even when the reaction was conducted with 5.0 equiv of added water.

TABLE 2

Intramolecular Hydroamination of Secondary Aminoalkenes

| Entry | Aminoalkene | Product | Yield (%) |
|---|---|---|---|
| 1 | (structure with NHMe) | (pyrrolidine with Me) | 90$^a$ |
| 2 | (structure with NH-CH$_2$-cyclohexyl) | (pyrrolidine product) | 91 |
| 3 | Ar = Phenyl | | 91 |
| 4 | Ar = 4-C$_6$H$_4$Cl | | 99 |
| 5 | Ar = 4-C$_6$H$_4$OMe | | 98 |
| 6 | Ar = 4-C$_6$H$_4$CN | | 85 |
| 7 | Ar = 4-C$_6$H$_4$CO$_2$Me | | 94 |
| 8 | (structure with NHBn) | (pyrrolidine with Bn) | 83 |
| 9 | (cyclohexyl structure with NHBn) | (spiro pyrrolidine with Bn) | 92 |
| 10 | (structure with NHBn and HO) | (pyrrolidine with Bn, HO) | 65 (11:1) |
| 11 | (structure with NHBn) | (pyrrolidine with Bn) | 64 |

TABLE 2-continued

Intramolecular Hydroamination of Secondary Aminoalkenes

| Entry | Aminoalkene | Product | Yield (%) |
|---|---|---|---|
| 12 | 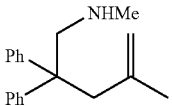 | 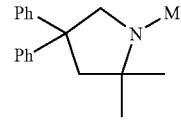 | 96 |
| 13 | 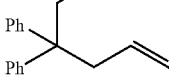 | 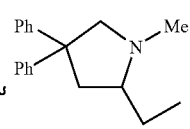 | 76[b] |
| 14 | 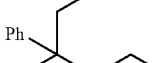 | 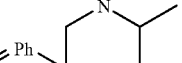 | 86[b] |

[a]1 mol % of rhodium complex and 1.2 mol % L2 were employed.
[b]5 mol % of rhodium complex and 6 mol % of L2 were used, and reaction was run at 100° C.

It has been reported that geminal disubstitution facilitates intramolecular hydroamination (Curtin, M. L. et al., *J. Org. Chem.* 1990, 55, 5278). However, even substrates lacking substituents between the alkene and the amine underwent cyclization in the presence of the composition generated from [Rh(COD)$_2$]BF$_4$ and L2. For example, N-benzyl-5-aminopentene cyclized to form the corresponding pyrrolidine in 64% yield (Table 2, entry 11).

Successful reactions of amines with disubstituted alkenes have been limited. Surprisingly, cyclization of the 1,1-disubstituted alkene in entry 12 of Table 2 occurred in excellent yield. Even more challenging is the reaction of amines with internal alkenes. No previous late metal composition has led to the addition of an N—H bond of an amine across an internal alkene. Surprisingly, the reaction of the 1,2-disubstituted aminoalkene in entry 13 of Table 2 occurred in good yield at 100° C.

Most of the reactions listed in Table 2 yielded hydroaminated products that included a five-membered ring. However, reaction with the composition also led to cyclizations to form six-membered rings in high yields, as shown by the example in entry 14 of Table 2.

Figure 3:
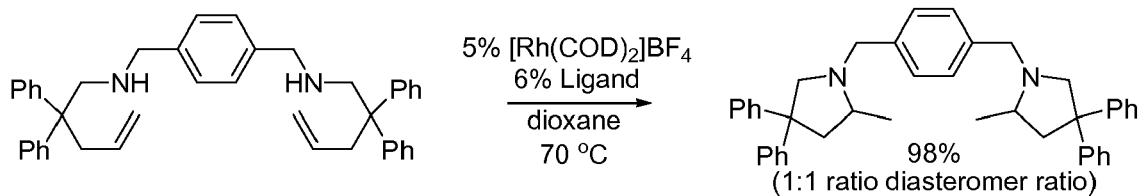
FIG. 3 represents chemical structures and a reaction scheme for an example of hydroamination of the aminoalkene substrate N-{4-[(2,2-diphenylpent-4-enylamino)methyl]benzyl}-2,2-diphenylpent-4-en-1-amine.

In addition to the reactions listed in Table 2, the scope of the hydroamination of 5- and 6-N-alkyl aminoalkenes to form nitrogen heterocycles was illustrated by performing two sequential hydroaminations. FIG. 3 represents chemical structures and a reaction scheme for an example of hydroamination of the aminoalkene substrate N-{4-[(2,2-diphenylpent-4-enylamino)methyl]benzyl}-2,2-diphenylpent-4-en-1-amine, using rhodium complex [Rh(COD)$_2$]BF$_4$ and ligand L2. A doubly hydroaminated product was achieved in excellent yield.

Table 3 represents chemical structures of substrates, their corresponding hydroaminated products, and reaction yields for a variety of hydroamination reactions in which the amino group is a primary amino group. Unless otherwise specified, the reaction mixtures were formed with 0.5 mmol of the aminoalkene, 5 mol % of rhodium complex [Rh(COD)$_2$]BF$_4$, 6 mol % of L2 and 0.5 mL of dioxane, and the reaction mixtures were heated at 100° C. for 10 hours. Experimental details are provided in Example 4. The yields listed in Table 3 are isolated yields, except where noted.

TABLE 3

Intramolecular Hydroamination of Primary Aminoalkenes

| Entry | Aminoalkene | Product | Yield (%) |
|---|---|---|---|
| 1 | 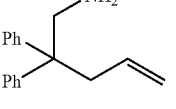 | 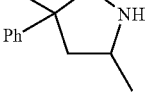 | 83 |
| 2 | 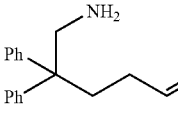 | 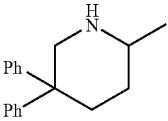 | 84 |
| 3 | 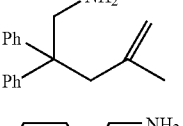 |  | 96[a] |
| 4 | 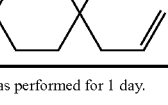 | 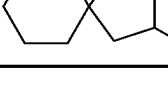 | 74[b] |

[a]Reaction was performed for 1 day.
[b]NMR yield.

The reactions listed in Table 3 helped to illustrate further the scope of the hydroamination reaction. The composition generated from 5 mol % [Rh(COD)$_2$]BF$_4$ and 6 mol % of L2 provided for the formation of a hydroamination product from aminoalkenes containing primary amine units. The primary aminoalkenes cyclized to form five- and six-membered rings in good yields. These results are surprising and unexpected, since no late transition metal has ever been reported to catalyze the addition of primary alkylamines across alkenes.

The following examples are provided to illustrate one or more preferred embodiments of the invention. Numerous variations may be made to the following examples that lie within the scope of the invention.

EXAMPLES

General Procedures. All manipulations were conducted under an inert atmosphere using a nitrogen-filled glovebox (INNOVATIVE TECHNOLOGIES, Newburyport, Mass.) equipped with an oxygen sensor (working oxygen level <2.0 ppm) and low-temperature refrigeration unit (−35° C.). All reactions were conducted in flame- or oven-dried round-bottomed flasks fitted with rubber septa under a positive pressure of argon, or in 1-dram vials fitted with a Teflon-lined screw cap (13-mm diameter, 425 GPI thread; QORPAK, Bridgeville, Pa.) under an atmosphere of nitrogen, unless otherwise noted. Organic solutions were concentrated by rotary evaporation at 25-40° C. Analytical thin-layer chromatography (TLC) was performed using glass plates pre-coated with silica gel (0.25 mm, 60 Å pore size) impregnated with a fluorescent indicator (254 nm). TLC plates were visualized by exposure to ultraviolet light (UV) and/or submersion in aqueous ceric ammonium molybdate solution (CAM) or aqueous potassium permanganate solution (KMnO$_4$), followed by brief heating on a hot plate (175° C., 10-15 s).

Materials. THF and diethyl ether were obtained as HPLC grade without inhibitors. Benzene, toluene, dichloromethane, and acetonitrile were obtained as ACS reagent grade. THF, diethyl ether, benzene, toluene, and dichloromethane were degassed by purging with nitrogen for 45 min and dried with a solvent purification system containing a 1 meter column containing activated alumina. Anhydrous 1,4-dioxane was obtained from ALDRICH (St. Louis, Mo.) and used without further purification. 1,4-Dioxane-$d_8$ was dried over appropriate drying agents and vacuum transferred prior to use. The rhodium complexes and 2-dicyclohexyl-phosphino-2'-(N,N-dimethylamino)biphenyl (L2) were used as received from STREM.

Instrumentation. $^1$H NMR spectra were obtained at 400 or 500-MHz and recorded relative to residual protio-solvent. $^{13}$C NMR spectra were obtained at 100 or 125 MHz, and chemical shifts were recorded relative to the solvent resonance. $^{31}$P NMR spectra were obtained at 122, 162 or 202 MHz, and chemical shifts are reported relative to 85% $H_3PO_4$. Analytical gas chromatography (GC) was performed using a HEWLETT-PACKARD 5890 Gas Chromatograph fitted with a flame ionization detector.

Example 1

Synthesis of 4,5-(Bis[bis-diethylamido]phosphonito)-9,9-dimethylxanthene (L1)

This compound was prepared according to Goertz, W. et al. *Chem. Eur. J.* 7, 1614, 2001. $^1$H NMR (500 MHz, CDCl$_3$): δ 1.02 (t, J=7.0 Hz, 24H), 1.60 (s, 6H), 3.05-3.12 (m, 16H), 7.05 (t, J=7.5 Hz, 2H), 7.33-7.36 (m, 4H); $^{13}$C NMR (125 Hz, CDCl$_3$): δ 14.6, 33.2, 34.1, 43.3, 122.2, 125.9, 129.5, 130.0, 130.7, 150.7; $^{31}$P{1H} NMR (202 MHz, CDCl$_3$): δ 90.9 (s).

Example 2

Synthesis of Alkenamines 2,2-Diphenylpent-4-en-1-amine was prepared according to Bender, C. F. et al. *J. Am. Chem. Soc.* 127, 1070, 2005. $^1$H NMR (400 MHz, CDCl$_3$) δ 0.87 (s, 2H), 2.95 (d, J=7.2 Hz, 2H), 3.34 (s, 2H), 4.99 (dt, J=10.0, 0.8 Hz, 1H), 5.07 (dd, J=17.2, 2.0 Hz, 1H), 5.10-5.46 (m, 1H), 7.19-7.32 (m, 10H); $^{13}$C NMR (100 MHz, CDCl$_3$) δ 41.4, 48.8, 51.6, 118.0, 126.3, 128.3, 128.4, 134.9, 146.5.

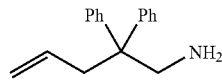

4-Methyl-2,2-diphenylpent-4-en-1-amine was prepared according to Molander, G. A. et al. *J. Org. Chem.* 63, 8983, 1998. $^1$H NMR (400 MHz, CDCl$_3$) δ 0.87 (s, 2H), 1.07 (s, 3H), 2.93 (s, 2H), 3.42 (s, 2H), 4.60 (d, J=0.8 Hz, 1H), 4.83 (t, J=2.0 Hz, 1H), 7.17-7.30 (m, 10H); $^{13}$C NMR (100 MHz, CDCl$_3$) δ 24.6, 44.2, 48.0, 51.5, 115.5, 126.3, 128.2, 128.6, 143.1, 147.2.

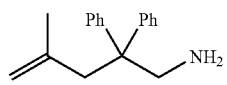

2,2-Diphenylhex-5-en-1-amine was prepared according to Kondo, T. et al. *J. Am. Chem. Soc.* 124, 186, 2002. $^1$H NMR (400 MHz, CDCl$_3$) δ 0.82 (s, 2H), 1.76-1.82 (m, 2H), 2.21-2.25 (m, 2H), 3.36 (s, 2H), 4.92-5.01 (m, 2H), 5.74-5.83 (m, 1H), 7.19-7.33 (m, 10H); $^{13}$C NMR (100 MHz, CDCl$_3$) δ28.8, 36.0, 49.3, 52.0, 114.6, 126.3, 128.3, 128.5, 139.1, 146.6.

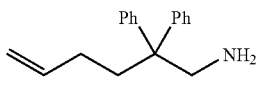

(1-Allylcyclohexyl)methanamine was prepared according to Bender, C. F. et al. *J. Am. Chem. Soc.* 127, 1070, 2005. $^1$H NMR (400 MHz, CDCl$_3$) δ 0.94 (s, 2H), 1.16-1.38 (m, 11H), 2.01 (d, J=7.6 Hz, 2H), 2.45 (s, 2H), 4.96 (s, 1H), 5.00 (d, J=6.4 Hz, 1H), 5.68-5.77 (m, 1H); $^{13}$C NMR (100 MHz, CDCl$_3$) δ 21.7, 26.6, 33.4, 37.2, 40.0, 49.0, 117.0, 135.2.

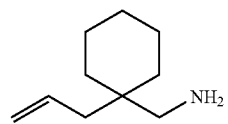

N-methyl-2,2-diphenylpent-4-en-1-amine was prepared according to Stubbert, B. D. et al. *J. Am. Chem. Soc.* 129, 4253, 2007. $^1$H NMR (400 MHz, CDCl$_3$) δ 0.49 (s, 1H), 2.38 (s, 3H), 3.01 (d, J=6.8 Hz, 2H), 3.18 (s, 2H), 4.95-5.08 (m, 2H), 5.35-5.45 (m, 1H), 7.19-7.32 (m, 10H); $^{13}$C NMR (100 MHz, CDCl$_3$) δ 37.5, 42.1, 50.3, 58.9, 117.9, 126.2, 128.2, 128.3, 135.1, 146.9.

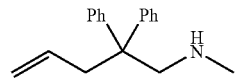

N-(Cyclohexylmethyl)-2,2-diphenylpent-4-en-1-amine was prepared from 2,2-diphenylpent-4-enylamine and cyclohexanecarboxaldehyde according to the procedure used for preparation of N-benzyl-2,2-diphenylpent-4-en-1-amine. The product was obtained in a 97% yield as a colorless oil. The compound was purified by column chromatography on silica gel (Hexane/Ethyl acetate=8/1). $^1$H NMR (400 MHz, CDCl$_3$) δ 0.41 (s, 1H), 0.74-0.83 (m, 2H), 1.08-1.41 (m, 4H), 1.59-1.71 (m, 5H), 2.38 (d, J=6.8 Hz, 2H), 3.05 (d, J=6.8 Hz, 2H), 3.20 (s, 2H), 4.97 (dt, J=10.4, 0.12 Hz, 1H), 5.06 (dt, J=16.8, 1.2 Hz, 1H), 5.36-5.47 (m, 1H), 7.19-7.33 (m, 10H); $^{13}$C NMR (100 MHz, CDCl$_3$) δ 26.3, 27.1, 31.6, 37.7, 41.9, 50.4, 56.3, 57.5, 117.8, 126.1, 128.2, 123.3, 135.3, 147.3.

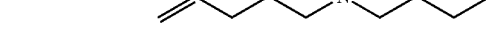

N-Benzyl-2,2-diphenylpent-4-en-1-amine was prepared according to Bender, C. F. et al. *J. Am. Chem. Soc.* 127, 1070, 2005. The compound was obtained in 98% yield as a colorless oil. $^1$H NMR (400 MHz, CDCl$_3$) δ 1.00 (s, 1H), 3.09 (d, J=7.2 Hz, 2H), 3.25 (s, 2H), 3.77 (s, 2H), 4.95 (dt, J=10.0, 0.12 Hz, 1H), 5.04 (dt, J=16.0, 1.2 Hz, 1H), 5.34-5.45 (m, 1H), 7.19-7.35 (m, 15H); $^{13}$C NMR (100 MHz, CDCl$_3$) δ 41.9, 50.4, 54.4, 55.5, 117.9, 126.2, 127.0, 128.2, 128.3, 128.4, 128.5, 135.1, 140.9, 147.1.

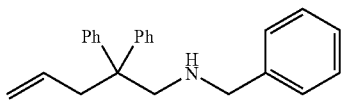

N-(4-Chlorobenzyl)-2,2-diphenylpent-4-en-1-amine was prepared according to Ackermann, L. et al. *Org. Biomol. Chem.* 5, 1975, 2007. The compound was obtained in 95% yield as a colorless oil. $^1$H NMR (400 MHz, CDCl$_3$) δ 0.89 (s, 1H), 3.07 (d, J=7.2 Hz, 2H), 3.21 (s, 2H), 3.71 (s, 2H), 4.92-5.05 (m, 2H), 5.31-5.42 (m, 1H), 7.15-7.32 (m, 14H); $^{13}$C NMR (100 MHz, CDCl$_3$) δ41.8, 50.3, 53.6, 54.4, 117.9, 126.3, 128.2, 128.3, 128.6, 129.5, 132.6, 135.1, 139.4, 147.0.

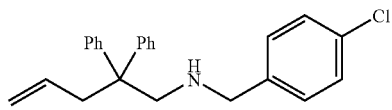

N-(4-methoxybenzyl)-2,2-diphenylpent-4-en-1-amine was prepared according to Bender, C. F. et al. *J. Am. Chem. Soc.* 127, 1070, 2005. The compound was obtained in 94% yield as a colorless oil. $^1$H NMR (400 MHz, CDCl$_3$) δ 0.91 (s, 1H), 3.09 (d, J=7.2 Hz, 2H), 3.24 (s, 2H), 3.70 (s, 2H), 3.82 (s, 3H), 4.95 (dt, J=10.0, 1.2 Hz, 1H), 5.06 (dt, J=17.2, 1.2 Hz, 1H), 5.34-5.45 (m, 1H), 6.85-6.89 (m, 2H), 7.16-7.33 (m, 12H); $^{13}$C NMR (100 MHz, CDCl$_3$) δ 41.9, 50.4, 53.8, 55.4, 55.5, 113.8, 117.9, 126.2, 128.2, 128.3, 129.3, 133.1, 135.2, 147.1, 158.7.

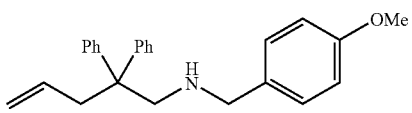

4-[(2,2-Diphenylpent-4-enylamino)methyl]benzonitrile was prepared according to Bender, C. F. et al. *J. Am. Chem. Soc.* 127, 1070, 2005. The compound was obtained in 94% yield as a colorless oil. $^1$H NMR (400 MHz, CDCl$_3$) δ 0.96 (s, 1H), 3.06 (d, J=7.2 Hz, 2H), 3.19 (s, 2H), 3.78 (s, 2H), 4.92 (dd, J=10.4, 2.0 Hz, 1H), 4.99 (dt, J=17.6, 1.2 Hz, 1H), 5.28-5.39 (m, 1H), 7.16-7.35 (m, 12H), 7.99 (d, J=8.4 Hz, 2H); $^{13}$C NMR (100 MHz, CDCl$_3$) δ 41.8, 50.3, 53.9, 55.5, 110.7, 118.0, 119.4, 126.4, 128.2, 128.3, 128.7, 132.3, 135.0, 146.7, 146.8.

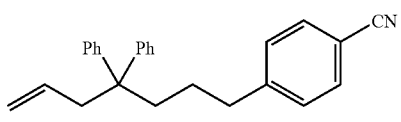

Methyl 4-[(2,2-diphenylpent-4-enylamino)methyl]benzoate was prepared according to Bender, C. F. et al. *J. Am. Chem. Soc.* 127, 1070, 2005. The compound was obtained in 92% yield as a colorless oil. $^1$H NMR (400 MHz, CDCl$_3$) δ 0.97 (s, 1H), 3.08 (d, J=7.2 Hz, 2H), 3.21 (s, 2H), 3.79 (s, 2H), 3.92 (s, 3H), 4.93 (dd, J=10.0, 2.0 Hz, 1H), 5.03 (dt, J=16.8, 1.2 Hz, 1H), 5.30-5.39 (m, 1H), 7.17-7.32 (m, 12H), 7.99 (dd, J=7.2, 1.2 Hz, 2H); $^{13}$C NMR (100 MHz, CDCl$_3$) δ 41.8, 50.3, 52.3, 54.0, 55.5, 118.0, 126.3, 128.1, 128.2, 128.3, 128.3, 128.9, 129.8, 135.0, 146.5, 146.9, 167.3.

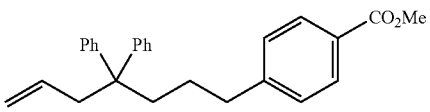

N-Benzyl-2,2-dimethylpent-4-en-1-amine was prepared according to Bender, C. F. et al. *J. Am. Chem. Soc.* 127, 1070, 2005. The compound was obtained in 96% yield as a colorless oil. $^1$H NMR (500 MHz, CDCl$_3$) δ 0.92 (s, 6H), 1.10 (s, 1H), 2.05 (d, J=7.5 Hz, 2H), 2.39 (s, 2H), 3.81 (s, 2H), 5.01-5.06 (m, 2H), 5.78-5.87 (m, 1H), 7.25-7.37 (m, 5H); $^{13}$C NMR (125 MHz, CDCl$_3$) δ 25.7, 34.6, 44.8, 54.9, 59.9, 117.0, 127.0, 128.2, 128.5, 135.9, 141.3.

(1-Allylcyclohenxyl)-N-benzyl-methanamine was prepared according to Bender, C. F. et al. *J. Am. Chem. Soc.* 127, 1070, 2005. The compound was obtained in 97% yield as a colorless oil. $^1$H NMR (400 MHz, CDCl$_3$) δ 1.17 (s, 1H), 1.13-1.49 (m, 10H), 2.14 (d, J=7.6 Hz, 2H), 2.43 (s, 2H), 3.79 (s, 2H), 5.00-5.07 (m, 2H), 5.74-5.86 (m, 1H), 7.23-7.37 (m, 5H); $^{13}$C NMR (100 MHz, CDCl$_3$) δ 21.8, 26.7, 34.2, 36.9, 40.9, 54.9, 56.1, 116.9, 126.9, 128.2, 128.5, 135.6, 141.3.

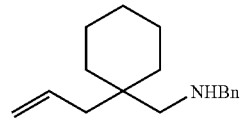

1-{1-[(Benzylamino)methyl]-cyclohexyl}prop-2-en-1-ol was prepared according to Bender, C. F. et al. *J. Am. Chem. Soc.* 127, 1070, 2005. The compound was obtained in 81% yield as a colorless oil. $^1$H NMR (400 MHz, CDCl$_3$) δ 1.20-1.71 (m, 12H), 2.65 (d, J=12.4 Hz, 1H), 2.75 (d, J=12.0 Hz, 1H), 3.72 (s, 2H), 4.06 (d, J=5.2 Hz, 1H), 5.16 (dd, J=10.4, 2.0 Hz, 1H), 5.28 (d, 16.0 Hz, 1H), 5.85-5.94 (m, 1H), 7.24-7.35 (m, 5H); $^{13}$C NMR (100 MHz, CDCl$_3$) δ 21.6, 26.5, 31.5, 39.3, 54.4, 54.7, 80.4, 116.0, 127.5, 128.5, 128.7, 138.6, 139.4.

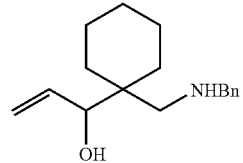

N-Benzylpent-4-en-1-amine was prepared according to Gribkov, D. V. et al. *Angew. Chem. Int. Ed. Engl.* 43, 5542, 2004. The compound was obtained in 85% yield as a colorless oil. $^1$H NMR (500 MHz, CDCl$_3$) δ 1.48 (s, 1H), 1.62 (quint, J=7.5 Hz, 2H), 2.11 (q, J=7.0 Hz, 2H), 2.65 (t, J=7.0 Hz, 2H), 3.79 (s, 2H), 4.96 (dd, J=10.5, 1.0 Hz, 1H), 5.02 (dd, J=17.0, 1.5 Hz, 1H), 5.79-5.84 (m, 1H), 7.25-7.34 (m, 5H); $^{13}$C NMR (125 MHz, CDCl$_3$) δ 29.5, 31.8, 49.1, 54.2, 114.9, 127.1, 128.3, 128.6, 138.7, 140.7.

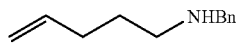

N,4-Dimethyl-2,2-diphenylpent-4-en-1-amine was obtained from 4-methyl-2,2-diphenylpent-4-en-1-amine and ethylformate according to the procedure used for preparation of N-methyl-2,2-diphenylpent-4-en-1-amine. The product was obtained in a 90% yield as a colorless oil. The compound was purified by column chromatography on silica gel (Hexane/Ethyl acetate=5/1). $^1$H NMR (400 MHz, CDCl$_3$) δ 0.47 (s, 1H), 1.09 (s, 3H), 2.37 (s, 3H), 3.01 (s, 2H), 3.25 (s, 2H), 4.61 (d, J=1.6 Hz, 1H), 4.84 (dd, J=2.8, 1.2 Hz, 1H), 7.17-7.31 (m, 10H); $^{13}$C NMR (100 MHz, CDCl$_3$) δ 24.7, 37.2, 44.7, 50.3, 58.0, 115.4, 126.2, 128.2, 128.4, 143.2, 147.6.

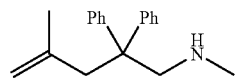

(E)-N-Methyl-2,2-diphenylhex-4-en-1-amine and (Z)—N-Methyl-2,2-diphenylhex-4-en-1-amine were obtained as a mixture in 96% yield as a colorless oil, according to the procedure used for the preparation of N-methyl-2,2-diphenylpent-4-en-1-amine. The compound was purified by column chromatography on silica gel (Hexane/Ethyl acetate=5/1). $^1$H NMR (500 MHz, CDCl$_3$) δ 0.76 (s, 1H), 0.93 (d, J=6.5 Hz, 0.2H), 1.55 (d, J=6.5 Hz, 2.8H), 2.29 (s, 0.2H), 2.36 (s, 2.8H), 2.91 (d, J=7.0 Hz, 2H), 3.15 (s, 2H), 4.98-5.02 (m, 1H), 5.41-5.46 (m, 1H), 7.17-7.30 (m, 10H); $^{13}$C NMR (125 MHz, CDCl$_3$) δ 18.3, 37.5, 40.9, 50.5, 58.9, 127.1, 128.1, 128.3, 128.4, 147.1.

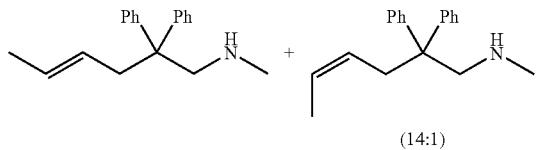

(14:1)

N-Benzyl-2,2-diphenylhex-5-en-1-amine was obtained from 2,2-diphenylhex-5-en-1-amine and benzaldehyde according to the procedure used for the preparation of N-benzyl-2,2-diphenylpent-4-en-1-amine. The compound was obtained in a 93% yield as a colorless oil. The compound was purified by column chromatography on silica gel (Hexane/Ethyl acetate=8/1). $^1$H NMR (400 MHz, CDCl$_3$) δ 1.04 (s, 1H), 1.66-1.73 (m, 2H), 2.53-2.40 (m, 2H), 3.24 (s, 2H), 3.77 (s, 2H), 4.91-5.00 (m, 2H), 5.75-5.86 (m, 1H), 7.19-7.34 (m, 15H); $^{13}$C NMR (100 MHz, CDCl$_3$) δ 28.9, 36.5, 50.5, 54.2, 55.4, 114.4, 126.2, 127.0, 128.1, 128.2, 128.3, 128.5, 139.4, 140.9, 147.3.

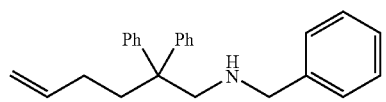

N-{4-[(2,2-diphenylpent-4-enylamino)methyl]benzyl}-2,2-diphenylpent-4-en-1-amine was obtained from 2,2-diphenylpent-4-enylamine and terephthaldicarboxaldehyde according to the procedure used for the preparation of N-benzyl-2,2-diphenylpent-4-en-1-amine. The compound was obtained in a 91% yield as a colorless oil. The compound was purified by column chromatography on silica gel (Hexane/Ethyl acetate=4/1). $^1$H NMR (400 MHz, CDCl$_3$) δ 0.86 (s, 2H), 3.05 (d, J=6.8 Hz, 4H), 3.20 (s, 4H), 3.70 (s, 4H), 4.90 (dd, J=12.8, 2.4 Hz, 2H), 5.00 (dt, J=17.2, 1.2 Hz, 2H), 5.31-5.38 (m, 2H), 7.12-7.28 (m, 24H); $^{13}$C NMR (100 MHz, CDCl$_3$) δ 41.8, 50.3, 54.1, 55.5, 117.9, 126.2, 128.0, 128.2, 128.3, 135.1, 139.3, 147.1.

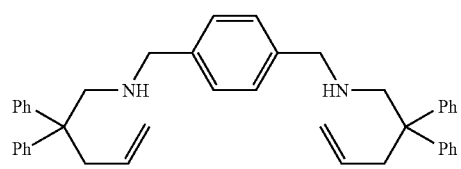

Example 3

General Procedure for the Hydroamination of Olefins with Secondary Alkylamines (Tables 1 and 2, and FIG. 3)

A mixture of the aminoalkene (0.50 mmol), [Rh(COD)$_2$]BF$_4$ (0.012 mmol, 5.1 mg) and L2 (0.015 mmol, 5.9 mg) in 0.50 mL of dioxane was allowed to stir at the temperature and time shown in Table 2. The resulting reaction mixture was washed with brine (20 mL) and extracted twice with CH$_2$Cl$_2$ (20 mL). The combined CH$_2$Cl$_2$ fractions were dried over Na$_2$SO$_4$ and concentrated under reduced pressure. The residue was purified by flash chromatography on silica gel to afford the desired product.

1,2-Dimethyl-4,4-diphenylpyrrolidine (A) was purified by flash chromatography on silica gel (washed with 2% Et$_3$N in hexane first, Hexane/Ethyl acetate=15/1) and obtained in a 90% yield (113 mg) as a colorless oil. $^1$H NMR (400 MHz, CDCl$_3$) δ 1.21 (d, J=5.6 Hz, 3H), 2.27 (dd, J=12.8, 7.6 Hz, 1H), 2.42 (s, 3H), 2.52-2.58 (m, 1H), 2.93 (d, J=9.7 Hz, 1H), 2.95 (dd, J=12.8, 7.6 Hz, 1H), 3.87 (d, J=9.7 Hz, 1H), 7.16-7.38 (m, 10H); $^{13}$C NMR (100 MHz, CDCl$_3$) δ 19.3, 40.8, 48.8, 52.9, 62.2, 70.7, 125.8, 126.1, 127.4, 127.7, 128.3, 128.5, 149.3, 151.0.

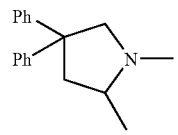

1-(Cyclohexylmethyl)-2-methyl-4,4-diphenylpyrrolidine was purified by flash chromatography on silica gel (Washed first with 2% Et$_3$N in hexane; Hexane/Ethyl acetate=20/1) and obtained in a 91% yield (152 mg) as a colorless oil. $^1$H NMR (500 MHz, CDCl$_3$) δ 0.91-1.00 (m, 2H), 1.11 (d, J=5.5 Hz, 3H), 1.21-1.32 (m, 3H), 1.52-1.55 (m, 1H), 1.71-1.78 (m, 4H), 2.05-2.17 (m, 3H), 2.53-2.58 (m, 1H), 2.63-2.67 (m, 1H), 2.82 (d, J=9.5 Hz, 1H), 2.85-2.89 (m, 1H), 3.87 (d, J=10 Hz, 1H), 7.15-7.35 (m, 10H); $^{13}$C NMR (125 MHz, CDCl$_3$) δ 19.9, 26.4, 26.6, 27.2, 32.1, 32.5, 37.6, 48.4, 53.0, 60.6, 61.7, 67.9, 125.6, 126.0, 127.6, 127.9, 128.1, 128.4, 149.2, 151.6; Anal. Calcd for C$_{24}$H$_{31}$N: C, 86.43; H, 9.37; N, 4.20 Found: C, 86.20; H, 9.67; N, 4.37.

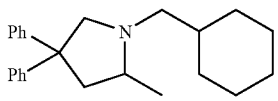

1-Benzyl-2-methyl-4,4-diphenylpyrrolidine was purified by flash chromatography on silica gel (Hexane/Ethyl acetate=20/1) and obtained in a 91% yield (151 mg) as a colorless oil. $^1$H NMR (400 MHz, CDCl$_3$) δ 1.24 (d, J=6.0 Hz, 3H), 2.80 (dd, J=12.8, 7.6 Hz, 1H), 2.85 (d, J=9.4 Hz, 1H), 2.86-2.94 (m, 1H), 2.99 (dd, J=12.6 Hz, 1H), 3.31 (d, J=13.6 Hz, 1H), 3.71 (d, J=9.4 Hz, 1H), 4.16 (d, J=13.6 Hz, 1H), 7.15-7.46 (m, 15H); $^{13}$C NMR (100 MHz, CDCl$_3$) δ 19.8, 48.3, 52.8, 58.3, 59.9, 66.8, 125.7, 126.1, 127.1, 127.6, 127.7, 128.1, 128.4, 128.5, 129.0, 140.4, 149.0, 151.0.

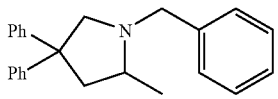

1-(4-Chlorobenzyl)-2-methyl-4,4-diphenylpyrrolidine was purified by flash chromatography on silica gel (Hexane/Ethyl acetate=20/1) and obtained in a 99% yield (179 mg) as a white solid. $^1$H NMR (500 MHz, CDCl$_3$) δ 1.24 (d, J=6.0 Hz, 3H), 2.31 (dd, J=13.0, 7.6 Hz, 1H), 2.85 (d, J=9.5 Hz, 1H), 2.87-2.93 (m, 1H), 3.00 (dd, J=13.0, 7.6 Hz, 1H), 3.30 (d, J=13.5 Hz, 1H), 3.69 (d, J=9.5 Hz, 1H), 4.11 (d, J=13.5 Hz, 1H), 7.15-7.37 (m, 14H); $^{13}$C NMR (125 MHz, CDCl$_3$) δ 19.8, 48.2, 52.9, 57.6, 59.9, 66.7, 125.8, 126.2, 127.5, 127.7, 128.2, 128.5, 128.7, 130.2, 132.7, 139.0, 148.9, 150.7; Anal. Calcd for C$_{24}$H$_{24}$ClN: C, 79.65; H, 6.68; N, 3.87 Found: C, 79.55; H, 6.63; N, 3.69.

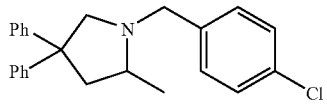

1-(4-Methoxybenzyl)-2-methyl-4,4-diphenylpyrrolidine was purified by flash chromatography on silica gel (Hexane/Ethyl acetate=20/1) and obtained in a 98% yield (175 mg) as a white solid. $^1$H NMR (400 MHz, CDCl$_3$) δ 1.24 (d, J=5.6 Hz, 3H), 2.27 (dd, J=12.8, 7.6 Hz, 1H), 2.83 (d, J=9.6 Hz, 1H), 2.84-2.91 (m, 1H), 3.00 (dd, J=12.8, 7.6 Hz, 1H), 3.26 (d, J=13.2 Hz, 1H), 3.71 (d, J=9.6 Hz, 1H), 3.87 (s, 3H), 4.11 (d, J=13.2 Hz, 1H), 6.95 (dd, J=6.4, 2.8 Hz, 2H), 7.16-7.38 (m, 12H); $^{13}$C NMR (100 MHz, CDCl$_3$) δ 19.8, 48.3, 52.7, 55.5, 57.6, 59.9, 66.6, 113.9, 125.7, 126.1, 127.5, 127.7, 128.1, 128.4, 130.0, 132.3, 149.1, 151.0, 158.8; Anal. Calcd for C$_{25}$H$_{27}$NO: C, 83.99; H, 7.61; N, 3.92 Found: C, 83.77; H, 7.65; N, 4.02.

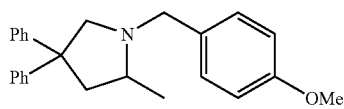

1-(4-Cyanobenzyl)-2-methyl-4,4-diphenylpyrrolidine was purified by flash chromatography on silica gel (Hexane/Ethyl acetate=15/1) and obtained in an 85% yield (150 mg) as a white solid. $^1$H NMR (400 MHz, CDCl$_3$) δ 1.20 (d, J=5.6 Hz, 3H), 2.27-2.32 (m, 1H), 2.85 (d, J=9.6 Hz, 1H), 2.86-2.98 (m, 2H), 3.38 (d, J=14.0, 1H), 3.62 (d, J=9.6 Hz, 1H), 4.12 (d, J=14.0 Hz, 1H), 7.14-7.32 (m, 10H), 7.50 (d, J=8.0 Hz, 2H), 7.63 (dd, J=8.0, 1.6 Hz, 2H); $^{13}$C NMR (100 MHz, CDCl$_3$) δ 19.8, 47.9, 52.9, 57.8, 59.9, 66.7, 110.8, 119.4, 125.9, 126.2, 127.3, 127.6, 128.2, 128.5, 129.3, 132.4, 146.4, 148.6, 150.4; Anal. Calcd for C$_{25}$H$_{24}$N$_2$: C, 85.19; H, 6.86; N, 7.95 Found: C, 85.14; H, 6.82; N, 7.99.

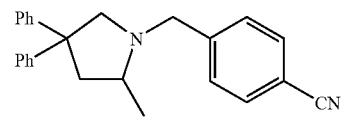

Methyl 4-(2-methyl-4,4-diphenylpyrrolidin-1-ylmethyl)-benzoate was purified by flash chromatography on silica gel (Hexane/Ethyl acetate=10/1) and obtained in a 94% yield (181 mg) as a white solid. $^1$H NMR (400 MHz, CDCl$_3$) δ 1.22 (d, J=6.0 Hz, 3H), 2.28 (dd, J=12.4, 7.6 Hz, 1H), 2.83 (d, J=10.0 Hz, 1H), 2.88-2.99 (m, 2H), 3.35 (d, J=13.6 Hz, 1H), 3.66 (d, J=9.6 Hz, 1H), 3.95 (s, 3H), 4.14 (d, J=13.6, 1H), 7.14-7.32 (m, 10H), 7.49 (d, J=8.4 Hz, 2H), 8.06 (d, J=8.0 Hz, 2H); $^{13}$C NMR (100 MHz, CDCl$_3$) δ 19.8, 48.1, 52.3, 52.8, 58.0, 60.1, 66.7, 125.8, 126.2, 127.4, 127.6, 128.2, 128.5, 128.7, 129.0, 129.9, 146.0, 148.8, 150.6, 167.4; Anal. Calcd for C$_{26}$H$_{27}$NO$_2$: C, 81.01; H, 7.06; N, 3.63 Found: C, 80.93; H, 7.02; N, 3.75.

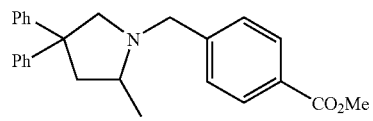

1-Benzyl-2,4,4-trimethylpyrrolidine was purified by flash chromatography on silica gel (washed with 2% Et$_3$N in hexane first, Hexane/Ethyl acetate=20/1) and obtained in an 83% yield (84 mg) as a colorless oil. $^1$H NMR (400 MHz, CDCl$_3$) δ 1.00 (s, 3H), 1.10 (s, 3H), 1.18 (d, J=6.0 Hz, 3H), 1.35 (dd, J=12.4 Hz, 1H), 1.74 (dd, J=12.4, 3.6 Hz, 1H) 1.96 (d, J=9.2 Hz, 1H), 2.52-2.68 (m, 1H), 2.67 (d, J=9.2 Hz, 1H), 3.13 (d, J=12.8 Hz, 1H), 4.05 (d, J=12.8 Hz 1H), 7.23-7.37 (m, 5H); $^{13}$C NMR (100 MHz, CDCl$_3$) δ 19.7, 29.5, 30.9, 35.6, 49.3, 58.3, 60.0, 68.6, 126.8, 128.3, 128.9, 140.3.

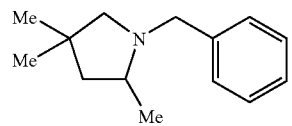

2-Benzyl-3-methyl-2-aza-spiro[4,5]decane was purified by flash chromatography on silica gel (washed with 2% Et$_3$N in hexane first, Hexane/Ethyl acetate=20/1) and obtained in a 92% yield (112 mg) as a colorless oil. $^1$H NMR (500 MHz, CDCl$_3$) δ 1.17 (d, J=6.0 Hz, 3H), 1.28-1.47 (m, 11H), 1.77 (dd, J=12.5, 7.6 Hz, 1H), 1.89 (d, J=9.5 Hz, 1H), 2.48-2.53 (m, 1H), 2.80 (d, J=9.0 Hz, 1H), 3.11 (d, J=13.0 Hz, 1H), 4.04 (d, J=13.5 Hz, 1H), 7.23-7.36 (m, 5H); $^{13}$C NMR (125 MHz, CDCl$_3$) δ 19.5, 23.7, 23.8, 26.3, 38.7, 39.4, 39.5, 47.1, 58.2, 59.2, 66.9, 126.8, 128.3, 128.9, 140.2.

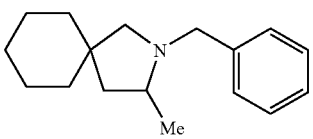

2-Benzyl-3-methyl-4-hydroxyl-2-aza-spiro[4,5]decane was purified by flash chromatography on silica gel (washed with 2% Et$_3$N in hexane first, Hexane/Ethyl acetate=5/1) and obtained in a 65% yield (84 mg) as a colorless oil. $^1$H NMR (500 MHz, CDCl$_3$) δ 1.20 (d, J=6.0 Hz, 3H), 1.28-1.56 (m, 10), 1.93 (d, J=9.5 Hz, 1H), 1.99 (d, J=11.0 Hz, 1H), 2.67-2.70 (m, 1H), 2.75 (d, J=9.5 Hz, 1H), 3.12 (d, J=13.0 Hz, 1H), 3.52 (dd, J=11.0, 3.5 Hz, 1H), 4.00 (d, J=13.5 Hz, 1H), 7.24-7.32 (m, 5H); $^{13}$C NMR (125 MHz, CDCl$_3$) δ 13.7, 23.3, 23.9, 26.1, 32.4, 37.8, 43.9, 57.5, 62.2, 64.4, 81.4, 127.0, 128.4, 128.9, 139.5.

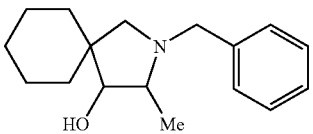

1-Benzyl-2-methylpyrrolidine was purified by flash chromatography on silica gel (washed with 2% Et$_3$N in hexane first, Hexane/Ethyl acetate=20/1) and obtained in a 64% yield (56 mg) as a colorless oil. $^1$H NMR (500 MHz, CDCl$_3$) δ 1.21 (d, J=6.0 Hz, 3H), 1.48-1.54 (m, 1H), 1.64-1.68 (m, 1H), 1.71-1.76 (m, 1H), 1.92-1.98 (m, 1H), 2.14 (q, J=9.0 Hz, 1H), 2.41-2.46 (m, 1H), 2.94 (td, J=9.0, 3.0 Hz, 1H), 3.19 (d, J=13.0 Hz, 1H), 4.05 (d, J=12.5 Hz, 1H), 7.24-7.36 (m, 5H); $^{13}$C NMR (125 MHz, CDCl$_3$) δ 19.2, 21.7, 32.9, 54.2, 58.5, 59.9, 127.1, 128.4, 129.4, 139.3.

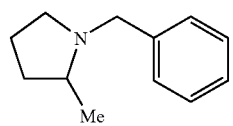

1,2,2-Trimethyl-4,4-diphenylpyrrolidine was purified by flash chromatography on silica gel (Hexane/Ethyl acetate=20/1) and obtained in a 96% yield (121 mg) as a colorless oil. $^1$H NMR (500 MHz, CDCl$_3$) δ 1.74 (s, 6H), 2.44 (s, 3H), 2.71 (s, 2H), 3.60 (s, 2H), 7.27 (t, J=7.5 Hz, 2H), 7.36-7.45 (m, 8H); $^{13}$C NMR (125 MHz, CDCl$_3$) δ 24.6, 34.6, 52.1, 54.7, 60.6, 67.6, 125.9, 127.5, 128.4, 150.4.

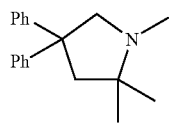

2-Ethyl-1-methyl-4,4-diphenylpyrrolidine was purified by flash chromatography on silica gel (Hexane/Ethyl acetate=20/1) and obtained in a 76% yield (96 mg) as a colorless oil. $^1$H NMR (500 MHz, CDCl$_3$) δ 0.92 (t, J=7.5 Hz, 3H), 1.26-1.33 (m, 1H), 1.72-1.77 (m, 1H), 2.23-2.38 (m, 2H), 2.39 (s, 3H), 2.87-2.92 (m, 2H), 3.84 (d, J=9.5 Hz, 1H), 7.12-7.35 (m, 10H); $^{13}$C NMR (125 MHz, CDCl$_3$) δ 11.1, 26.8, 41.2, 45.8, 52.8, 68.5, 70.4, 125.7, 126.1, 127.4, 127.6, 128.3, 128.4, 149.3, 150.8.

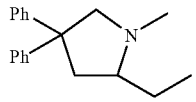

1-Benzyl-2-methyl-5,5-diphenylpiperidine was purified by flash chromatography on silica gel (Hexane/Ethyl acetate=20/1) and obtained in an 86% yield (147 mg) as a colorless oil. $^1$H NMR (400 MHz, CDCl$_3$) δ 1.26 (d, J=6.0 Hz, 3H), 1.46-1.56 (m, 1H), 1.71-1.78 (m, 1H), 2.31 (td, J=12.0, 3.2 Hz, 1H), 2.53-2.62 (m, 3H), 3.25 (d, J=13.2 Hz, 1H), 3.49 (d, J=12.4 Hz, 1H), 4.19 (d, J=13.2 Hz, 1H), 7.19-7.51 (m, 15H); $^{13}$C NMR (100 MHz, CDCl$_3$) δ 19.2, 31.3, 34.6, 46.9, 56.5, 59.2, 61.3, 125.7, 126.0, 127.3, 127.4, 128.0, 128.3, 128.4, 128.8, 129.9, 139.8, 147.1, 148.9.

1-{4-[(2-Methyl-4,4-diphenylpyrrolidin-1-yl)methyl]benzyl}-2-methyl-4,4-diphenylpyrrolidine, which was provided as a 1:1 mixture of diastereomers (according to $^{13}$C spectrum), was purified by flash chromatography on silica gel (Hexane/Ethyl acetate=5/1) and obtained in a 98% yield (282 mg) as a white solid. $^1$H NMR (500 MHz, CDCl$_3$) δ 1.25 (d, J=6.0 Hz, 6H), 2.28 (dd, J=13.0, 8.0 Hz, 2H), 2.84-2.90 (m, 4H), 2.99 (dd, J=13.0, 8.0 Hz, 2H), 3.31 (d, J=13.5 Hz, 2H), 3.74 (d, J=10.0 Hz, 2H), 4.16 (d, J=14.0 Hz, 2H), 7.16-7.40 (m, 24H); $^{13}$C NMR (125 MHz, CDCl$_3$) δ 19.8, 48.3, 48.4, 52.7, 58.0, 58.1, 59.9, 66.7, 66.8, 125.7, 126.1, 127.5, 127.6, 127.8, 128.1, 128.4, 128.7, 128.8, 138.8, 138.9, 149.1, 150.9, 151.0; Anal. Calcd for C$_{42}$H$_{44}$N$_2$: C, 87.45; H, 7.69; N, 4.86 Found: C, 87.43; H, 7.86; N, 5.02.

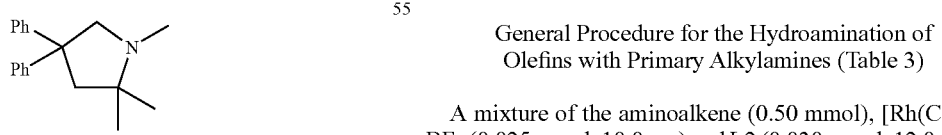

(1:1)

Example 4

General Procedure for the Hydroamination of Olefins with Primary Alkylamines (Table 3)

A mixture of the aminoalkene (0.50 mmol), [Rh(COD)$_2$]BF$_4$ (0.025 mmol, 10.0 mg) and L2 (0.030 mmol, 12.0 mg) in 0.50 mL of dioxane was allowed to stir at the temperature and time shown in Table 3. The resulting reaction mixture was washed with brine (20 mL) and extracted with CH$_2$Cl$_2$ (20 mL) twice. The combined CH$_2$Cl$_2$ fractions were dried over Na$_2$SO$_4$ and concentrated under reduced pressure. The residue was purified by flash chromatography on silica gel to afford the desired product.

2-Methyl-4,4-diphenylpyrrolidine was purified by flash chromatography on silica gel (washed with 2% Et$_3$N in hexane first, Hexane/Ethyl acetate=5/1) and obtained in an 83% yield (98 mg) as a colorless oil. $^1$H NMR (500 MHz, CDCl$_3$) δ 1.22 (d, J=6.5 Hz, 3H), 1.97 (s, 1H), 2.28 (dd, J=13.0, 9.0 Hz, 1H), 2.82 (dd, J=13.0, 6.5 Hz, 1H), 3.36-3.41 (m, 1H), 3.49 (d, J=11.5 Hz, 1H), 3.67 (dd, J=11.5, 1.5 Hz, 1H), 7.16-7.34 (m, 10H); $^{13}$C NMR (125 MHz, CDCl$_3$) δ 22.7, 47.3, 53.3, 57.5, 58.1, 126.2, 126.3, 127.2, 127.3, 128.5, 128.6, 147.4, 148.1.

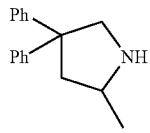

2-Methyl-5,5-diphenylpiperidine was purified by flash chromatography on silica gel (washed with 2% Et$_3$N in hexane first, Hexane/Ethyl acetate=5/1) and obtained in an 85% yield (107 mg) as a slightly yellow oil. $^1$H NMR (500 MHz, CDCl$_3$) δ 1.02 (d, J=6.5 Hz, 3H), 1.12-1.21 (m, 1H), 1.32 (s, 1H), 1.65 (dq, J=13.0, 3.5 Hz, 1H), 2.23 (td, J=13.0, 4.0 Hz, 1H), 2.72 (dq, J=13.0, 3.5 Hz, 1H), 2.76-2.81 (m, 1H), 3.13 (d, J=14.0 Hz, 1H), 3.92 (dd, J=13.5, 3.0 Hz, 1H), 7.11-7.26 (m, 6H), 7.36 (t, J=8.0 Hz, 2H), 7.43 (dd, J=8.5, 1.0 Hz, 2H); $^{13}$C NMR (125 MHz, CDCl$_3$) δ 22.7, 31.6, 35.6, 45.4, 52.5, 56.1, 126.0, 126.1, 126.7, 128.4, 128.5, 128.9, 145.0, 149.1.

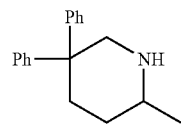

2,2-Methyl-4,4-diphenylpyrrolidine was purified by flash chromatography on silica gel (washed with 2% Et$_3$N in hexane first, Hexane/Ethyl acetate=5/1) and obtained in a 96% (120 mg) yield as a slightly yellow solid. $^1$H NMR (400 MHz, CDCl$_3$) δ 1.18 (s, 6H), 2.10 (s, 1H), 2.57 (s, 2H), 3.67 (s, 2H), 7.14-7.19 (m, 2H), 7.26-7.34 (m, 8H); $^{13}$C NMR (100 MHz, CDCl$_3$) δ 31.0, 52.3, 57.4, 58.6, 59.6, 126.2, 127.2, 128.7, 147.8.

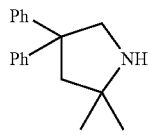

2,3-Dimethyl-2-aza-spiro[4,5]decane was obtained in a 74% NMR yield by using trimethoxybenzene as internal standard. $^1$H NMR (500 MHz, CDCl$_3$) δ 1.08 (dd, J=13.0, 9.5 Hz, 1H), 1.19 (d, J=6.0 Hz, 3H), 1.40-1.43 (m, 10H), 1.81 (dd, J=12.5, 6.5 Hz, 1H), 2.67 (d, J=11.0 Hz, 1H), 2.84 (d, J=11.5 Hz, 1H), 3.12 (s, 1H), 3.22-3.27 (m, 1H); $^{13}$C NMR (125 MHz, CDCl$_3$) δ 21.1, 23.7, 24.8, 26.2, 29.9, 37.2, 38.6, 44.0, 54.4, 58.5.

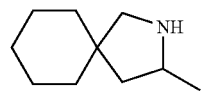

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:
1. A composition, comprising:
   a rhodium complex comprising
      a central rhodium atom,
      at least one ancillary ligand selected from the group consisting of cyclooctadiene, cyclooctene, acetonitrile and acetone, and
      a counterion selected from the group consisting of Cl$^-$, Br$^-$, AcO$^-$, TfO$^-$, CF$_3$CO$_2^-$, BF$_4^-$, ClO$_4^-$, ReO$_4^-$, AsF$_6^-$ and SbF$_6^-$, and
   an organic ligand, selected from the group consisting of 4,5-(bis[bis-diethylamido]-phosphonito-9,9-dimethylxanthene and 2-dicyclohexyl-phosphino-2'-(N,N-dimethylamino)-biphenyl.
2. The composition of claim 1, where the mole ratio of ligand to rhodium is from 0.8 to 2.
3. The composition of claim 1, where the mole ratio of ligand to rhodium is from 0.9 to 1.5.
4. The composition of claim 1, where the mole ratio of ligand to rhodium is from 1 to 1.2.
5. A catalyst, comprising:
   a rhodium complex selected from the group consisting of [Rh(COD)$_2$]BR$_4$, [Rh(MeCN)$_2$(COD)]BF$_4$, [Rh(COE)$_2$Cl]$_2$ and [Rh(COD)Cl]$_2$ and
   an organic ligand, selected from the group consisting of 4,5-(bis[bis-diethylamido]-phosphonito-9,9-dimethylxanthene and 2-dicyclohexyl-phosphino-2'-(N,N-dimethylamino)-biphenyl.

* * * * *

UNITED STATES PATENT AND TRADEMARK OFFICE
CERTIFICATE OF CORRECTION

PATENT NO. : 8,188,302 B2  Page 1 of 1
APPLICATION NO. : 12/251062
DATED : May 29, 2012
INVENTOR(S) : Liu et al.

It is certified that error appears in the above-identified patent and that said Letters Patent is hereby corrected as shown below:

In the Claims

Please replace in Claim 5, line 46, column 24 with, $[Rh(COD)_2]BF_4$, $[Rh(MeCN)_2(COD)]BF_4$, $[Rh$ Signed and Sealed this
Twenty-fourth Day of March, 2015

Michelle K. Lee
*Director of the United States Patent and Trademark Office*